United States Patent
Yamada et al.

[11] Patent Number: 6,058,764
[45] Date of Patent: May 9, 2000

[54] ANALYTICAL APPARATUS, LIQUID CHROMATOGRAPHY ANALYZER AND A METHOD THEREFOR

[75] Inventors: Yoshiaki Yamada, Tsuchiura; Kiyotoshi Mori, Hitachinaka; Masato Fukuda, Mito, all of Japan

[73] Assignee: Hitachi, Ltd., Tokyo, Japan

[21] Appl. No.: 09/152,697

[22] Filed: Aug. 24, 1998

[30] Foreign Application Priority Data

Aug. 28, 1997 [JP] Japan ................................. 9-232113

[51] Int. Cl.[7] .......................... B01D 15/08; G01N 1/10; G01N 30/02
[52] U.S. Cl. .................. 73/61.52; 73/61.59; 73/23.41; 73/23.36; 422/70; 436/161
[58] Field of Search ................. 73/61.52, 61.55, 73/61.59, 61.71, 61.56, 23.36, 23.41, 23.42; 436/161; 422/68.1, 70

[56] References Cited

U.S. PATENT DOCUMENTS

| | | | |
|---|---|---|---|
| 3,562,501 | 2/1971 | Mears | 235/151.35 |
| 3,649,203 | 3/1972 | Schneider | 23/253 R |
| 4,186,607 | 2/1980 | Porter et al. | 73/422 GC |
| 4,364,263 | 12/1982 | Sankoorikal et al. | 73/61.1 C |
| 4,849,110 | 7/1989 | Takata et al. | 210/656 |
| 4,991,428 | 2/1991 | Heyde | 73/61.1 C |
| 5,108,466 | 4/1992 | Klein et al. | 55/20 |
| 5,405,432 | 4/1995 | Snyder et al. | 95/82 |
| 5,468,643 | 11/1995 | Su et al. | 436/161 |
| 5,760,299 | 6/1998 | Johnson et al. | 73/61.56 |
| 5,801,302 | 9/1998 | Riviello et al. | 73/61.55 |
| 5,811,666 | 9/1998 | Yamada | 73/61.56 |

FOREIGN PATENT DOCUMENTS

| | | |
|---|---|---|
| 195 01 531 | 9/1995 | Germany . |
| WO91/06050 | 5/1991 | WIPO . |
| WO91/16675 | 10/1991 | WIPO . |

*Primary Examiner*—Hezron Williams
*Assistant Examiner*—J. David Wiggins
*Attorney, Agent, or Firm*—Kenyon & Kenyon

[57] ABSTRACT

A reliable analytical apparatus is provided which can produce a highly reliable analytical Value on the basis of data entered during manual sample preparation which can be easily traced and used in editing of the analytical result of the analyzer because they are stored in association with the results of measurements by the analyzer. The analytical apparatus has an input device for inputting sample preparation procedures through the display screen, and various computations based on weighed quantities, constant dilution volume and so on entered during the manual preparation, which are automatically executed so as to eliminate human error.

8 Claims, 7 Drawing Sheets

Sample Name : STD1
Analyzed Data and Time : 97/07/18 07:58
Volume : 4.0ul

Peak Quantitation : AREA

| No. | RT | Area | Name | Conc t mg/L | 8c |
|---|---|---|---|---|---|
| 4 | 2.15 | 157965 | Naphthal | 10.3 | W |
| 5 | 2.45 | 287030 | Anthrace | 10.2 | W |
| 6 | 2.91 | 57185 | Chrysene | 10.5 | W |
|  |  | 502180 |  | 31 |  |

Peak rejection level : 0

Sample PreParation Procedure :

ANALYTICAL APPARATUS, LIQUID CHROMATOGRAPHY ANALYZER AND A METHOD THEREFOR

BACKGROUND OF THE INVENTION

The present invention relates to an analytical apparatus including a liquid chromatography analyzer and a method therefor, and in particular, it relates to analysis which requires manual sample preparation by operators (hereinafter referred to as the manual method), and to an analytical apparatus which can store sample preparation procedures by the manual method associated with results of measurements by the analytical apparatus.

For the analytical apparatus such as liquid chromatograph, sample preparation for analysis is more or less automated; however, there are still many cases where samples must be prepared by the manual method. Since there is known no analytical apparatus that can provide data on its sample preparation when the manual method is used, the operator is required to carry out the following steps in order to be able to trace respective preparation procedures when obtaining analytical values of the samples: Namely, (1): record each preparation procedure as a flow chart in a notebook or the like, together with an actual value of weighed quantity, a constant volume of dilution, the serial number of equipment used, and so on; (2): use a calculator to find a concentration or a dilution ratio of a sample solution to be analyzed based on the actual value of weighed quantity, constant dilution volume and the like, and (3): obtain analytical values for a target sample from the values measured, dilution ratios and the like output from the analytical apparatus.

However, the prior art which is required to carry out the above-mentioned elaborate operation involves the following problems.

(1) Since the actual weighed value and the constant volume during the pretreatment operation required for obtaining the analytical value are obtained individually and separately from the output value from the analytical apparatus, a tedious work, for example, to paste an output chart from the analytical apparatus into the notebook is required for their recording and comparison.

(2) In order to obtain an analytical value, one must enter into the computer the actual weighed value, the constant volume and the like, which was already recorded in the notebook. Therefore, there is a possibility of human error in inputs by the operator, thereby degrading the reliability of the analyzed value.

Namely, since the prior art analytical apparatus is not supported for the sample preparation by the manual handling method, such manual elaboration as described above is required thereby preventing further improvement in the reliability of analysis.

SUMMARY OF THE INVENTION

The object of the invention is to provide an analytical apparatus in which sample preparation procedures can be traced easily and reliably, and which can obtain a highly reliable value of analysis.

The above-mentioned object of the invention is accomplished by providing an analytical apparatus which carries out analysis of manually prepared samples and which has at least a means for displaying the results of its analysis, wherein the display means is comprised of: a unit procedure region which displays each one of a plurality of procedures required in the sample preparation, which is presented as a picture symbol such as an icon; a sample preparation procedure display region which displays a combination of unit procedure regions to determine a sequence of steps for the sample preparation; and a detail information display region which is displayed on the screen in association with a specified unit procedure region and through which to enter and display data on a target preparation procedure; and wherein the analytical apparatus further comprises a data processing means which uses the data entered through the detail information display region to edit the result of the analysis of the samples.

Also, by selecting any one of the plurality of unit procedure regions, the content of the detail information display region associated with the selected preparation procedure will preferably be displayed.

Furthermore, character data from the detail information display region will preferably be displayed in the vicinity of each one of the unit procedure regions shown in the sample preparation procedure display region.

Moreover, the unit procedure regions displayed in the sample preparation procedure display region are connected to each other with lines in a time-series sequence of processing.

Still further, preferably, the above-mentioned data processing means calculates a concentration of the sample prepared on the basis of the data entered in the detail information display region in case its prepared sample is a standard sample.

Further, preferably, contents of the sample preparation procedure display region are displayed and output simultaneously together with the result of analysis of the analysis apparatus.

Further, preferably, the contents having been output as above are stored in the data processing means.

In other word, the feature of the invention is characterized in that a sample is prepared, a eluting liquid is supplied, a mixture solution is produced by mixing the prepared sample in the eluting liquid, the mixture solution is separated in a separation column, and a portion of the mixture solution having passed the separation column is detected, wherein the sample preparation is comprised of at least two steps, and any portion of steps in the at least two steps is displayed distinct from the -other portions of steps distinguishable from each other, and information related to its particular step and associated with the display is entered, then, on the basis of this information having been entered and an output from the detector, a result of analysis is output.

By provision of the above-mentioned means for use in the sample preparation procedures by the manual method, the actual sample value weighed and the constant volume quantity as well as data on the equipment used or the operator involved can be entered into the analytical apparatus. From this data having been entered, a concentration or a dilution ratio of the prepared sample can be automatically calculated. A calculated value is stored together with the result of analysis by the analytical apparatus, and is used, for example, for computation of a concentration of a feed liquid on the basis of the result of analysis and the dilution ratio calculated, as required. Since the sample preparation procedure data and the results of analysis by the analytical apparatus are stored together according to the invention, they can be easily traced. Further, since any calculation based on the actual weighed quantity of the sample and the value of the constant volume during sample preparation can be executed automatically from the input values input through the procedure input screen, thereby eliminating human input errors, and therefore an analytical apparatus which can produce a highly reliable analysis value can be provided.

DETAILED DESCRIPTION OF THE INVENTION

A preferred embodiment of the invention will be described by way of example of an analytical apparatus which uses a liquid chromatograph.

Figure 1:
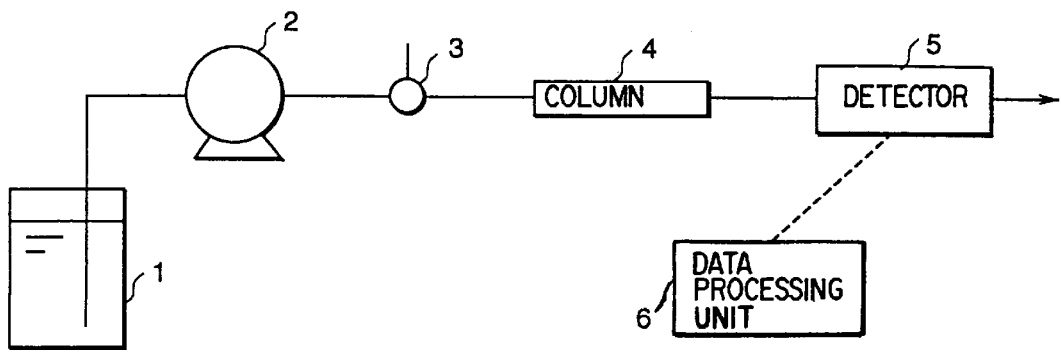
FIG. 1 is a schematic block diagram of a liquid chromatograph of the invention.

FIG. 1 is a schematic block diagram of a liquid chromatograph according to the invention. This liquid chromatograph is operated as follows.

A solution 1 is pumped toward an injection valve 3 by being pressurized and at a constant flow rate by pump 2. A prepared sample is injected through injection valve 3 into a flow passage to be sent to a liquid chromatography column 4 where the sample is separated per unit component. In a detector 5, any change in the solution is continuously measured and its signal is sent to a data processing unit 6. Signal values are plotted in time-series in data processing unit 6 to allow each component to be observed as having a peak. From a retention period of time of each peak (i.e., a delay time from sample injection), a qualitative test of each component is carried out. This will show a proportional relationship between the content of each component included in the injected sample and its peak area. Therefore, through both analysis of an unknown sample for which the concentration is not known and a standard sample for which the concentration is known, and from a ratio of peat areas between the results of analysis of both the samples as well as from the known concentration of the standard sample, it becomes possible to determine a concentration of the unknown sample.

Actually, before carrying out the analysis of the standard sample and the unknown sample, there are required operations such as weighing, pipetting and constant volume dilution for sample preparation. Some of these operations are automated; however, there are still many cases in which they are done manually by the operator. In the case where the manual handling method is used, the contents of manual operations carried out are displayed for use in the editing of data on the display screen of the data processing unit 6 according to the invention.

Figure 2:
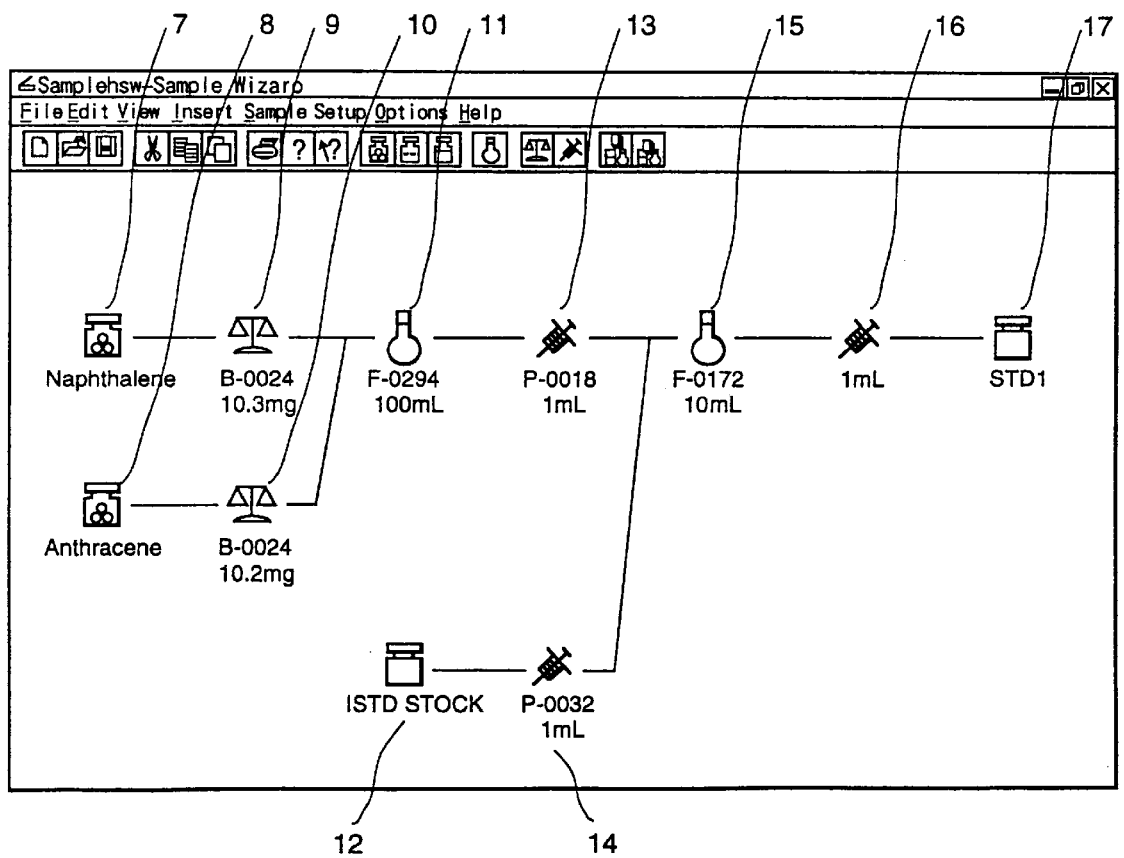
FIG. 2 is a diagram showing a sample preparation procedure input display screen of the invention.

FIG. 2 shows a manual method preparation procedure input screen (window) according to one embodiment of the invention. An example displayed on this screen indicates a preparation procedure for a standard sample (STD1). This procedure specifies that "naphthalene and anthracene be weighed to approximately 10 mg each and diluted in methanol to a constant volume of 100 ml. Then, 1 ml of this constant volume solution and 1 ml of an internal standard substance (chrysene solution) are injected into a measuring flask in which they are diluted to a constant volume of 10 ml. Approximately 1 ml of this prepared solution is injected into a sample bottle to be analyzed by liquid chromatograph."

As shown in FIG. 2, target components and frequently-used work contents are expressed as icons and always displayed on the preparation procedure input screen. The operator is thereby allowed to easily specify any particular preparation procedure bX clicking these icons with a pointing device (which is not shown) and sequentially arranging them on the screen. For example, in FIG. 2, different icons are used for an "individual component", a "weighing quantity", a "constant volume", "pipetting", and "solution". Namely, icons 7 and 8 indicate respective individual components, icons 9 and 10 indicate respective weighing quantities, icons 11 and 15 indicate respective constant volume quantities, icons 13, 14 and 16 indicate pipetting, and icons 12 and 17 indicate respective solutions.

Then, notes and remarks specific to and necessary for each icon can be written and displayed freely on the preparation procedure input screen. Namely, in FIG. 2, names of naphthalene and anthracene are written in and stored for individual component icons 7 and 8, respectively. For weighing quantity icons 9 and 10, weighed quantities 10.3 mg and 10.2 mg are entered and stored respectively associated with unit serial number B-0024 of a weighing balance used. For constant volume icons 11 and 15, respective constant volumes of dilution 100 ml and 10 ml are entered and stored associated with measuring flask unit numbers F-0294 and F-172. For solution icons 12 and 17, titles of ISTD STOCK and STD1 are entered and stored respectively. For pipetting icons 13 and 14, a pipetting quantity (1 ml) is entered and stored associated with unit numbers P-0018, P-0032 of measuring pipettes. Also, numeral 16 depicts a pipetting icon which, however, does not need a precise pipetting operation, with specific part ID accounting therefore, only a pipet quantity (1 ml) is entered and stored.

Figure 3:
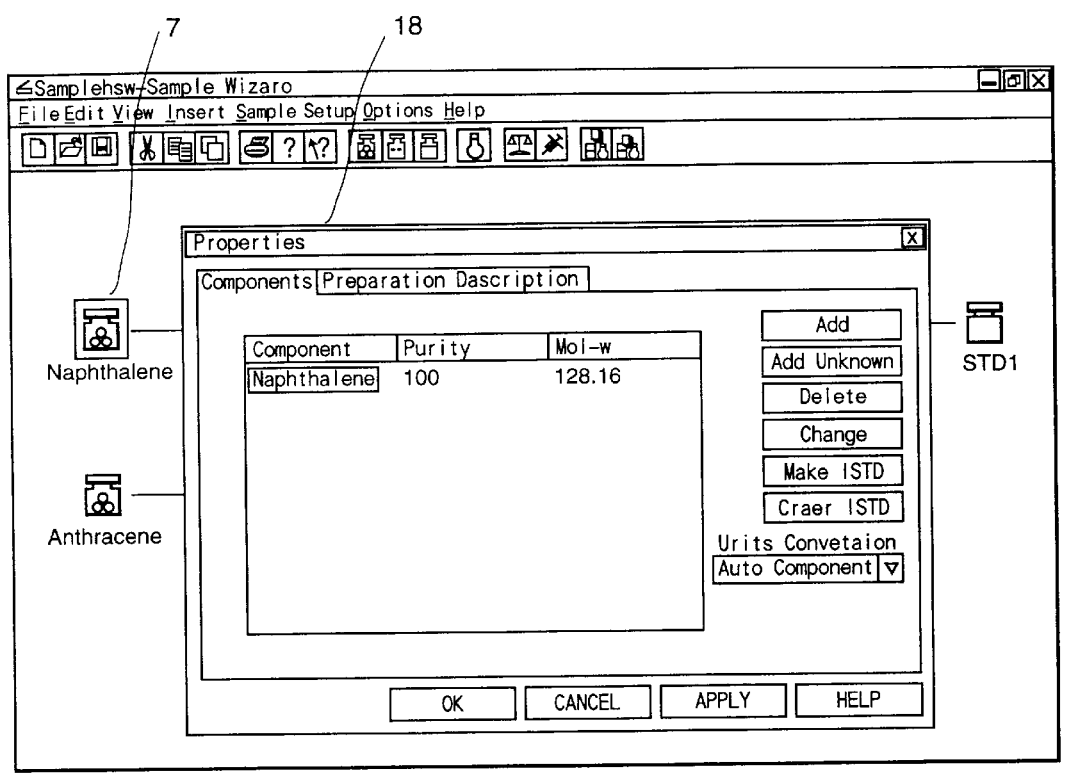
FIG. 3 is a diagram showing a detail data display screen for displaying detailed data on an individual component.

Now, with reference to FIG. 3, input procedures for inputting notes and remarks for each icon will be described. FIG. 3 is an example of a detailed data input screen for individual component icon 7. When an individual component icon 7 on the preparation procedure input screen is double-clicked, a detail display screen 18 associated thereto is displayed. Because this screen is the detail display screen of the individual component icon, it is allowed to enter a purity and a molecular weight (Mol-W) of its component therethrouqh. In an example of FIG. 3, purity 100 and molecular weight 128.16 of the component are entered and stored. Using these data items having been entered, data processing unit 6 can execute arithmetic operation, and it thus becomes possible to automatically compute changes in the weight and molar concentration of the standard sample to be displayed at the time of completion of the sample preparation.

Figure 4:
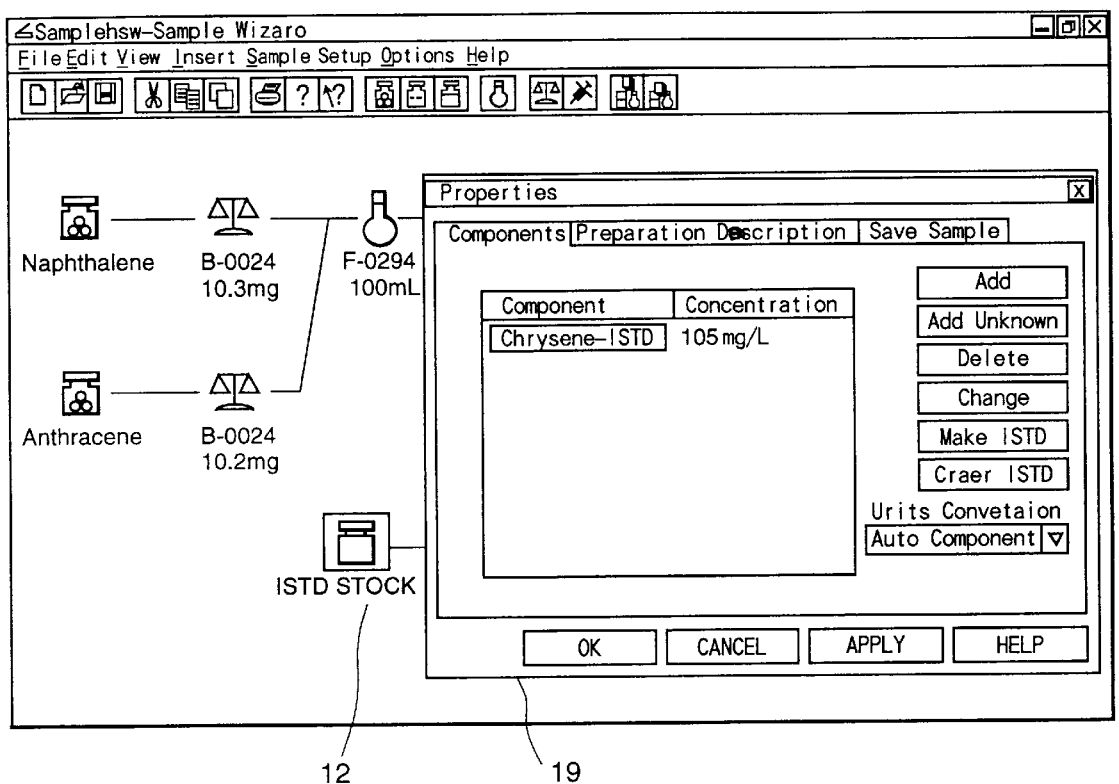
FIG. 4 is a diagram showing a detail data display screen for displaying detailed data on a solution.
Figure 5:
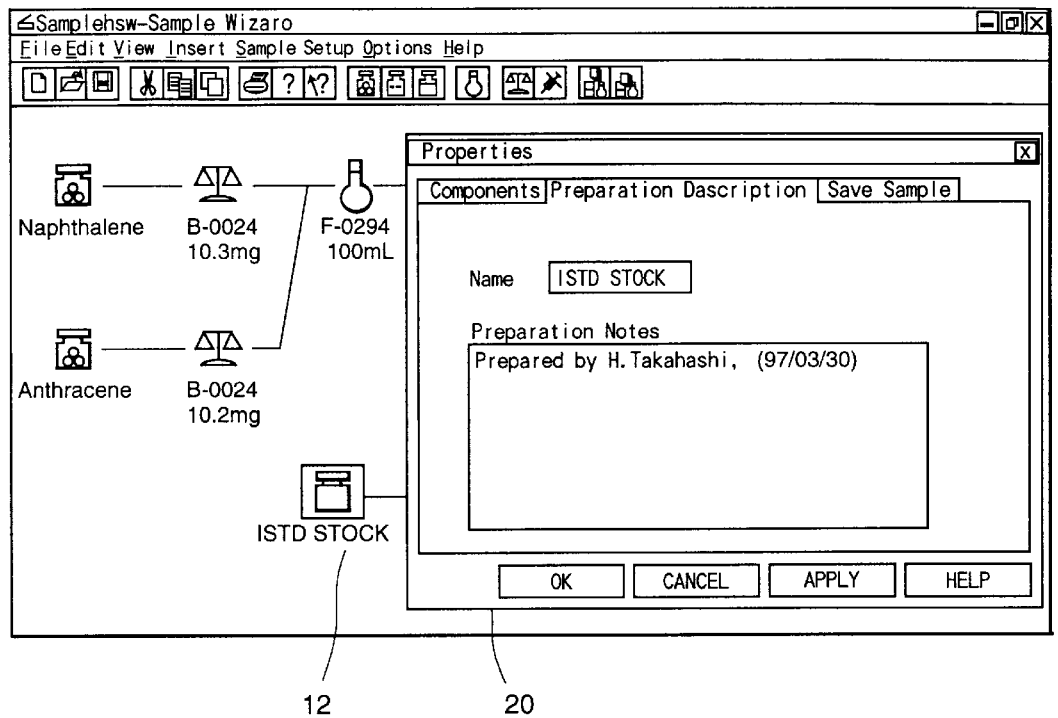
FIG. 5 is a diagram showing a detail data display screen for displaying detailed data on a solution.

Now, with reference to FIGS. 4 and 5, a detail input screen of the solution icon will be described. When solution icon 12 in the preparation procedure input screen is double-clicked, the detail display screen 19 associated thereto is displayed. Through the detail display screen 19 of the solution icon, it is allowed to enter the name of a component and its concentration. It this example, "chrysene" as its component, and "105 mg/L" as its concentration are entered and stored. Further, since this chrysene is used as an internal standard at the time of determination, legend "ISTD" indicative of the internal standard is entered and stored. Further, this detail display screen 19 can be switched to another detail display screen 20. In this another detail display screen 20, the name of the operator (H. Takahashi) who prepared the sample and the date of preparation (97/03/30) are entered and stored. Still further, the temperature and so on at the time of preparation are also entered and stored.

Figure 6:
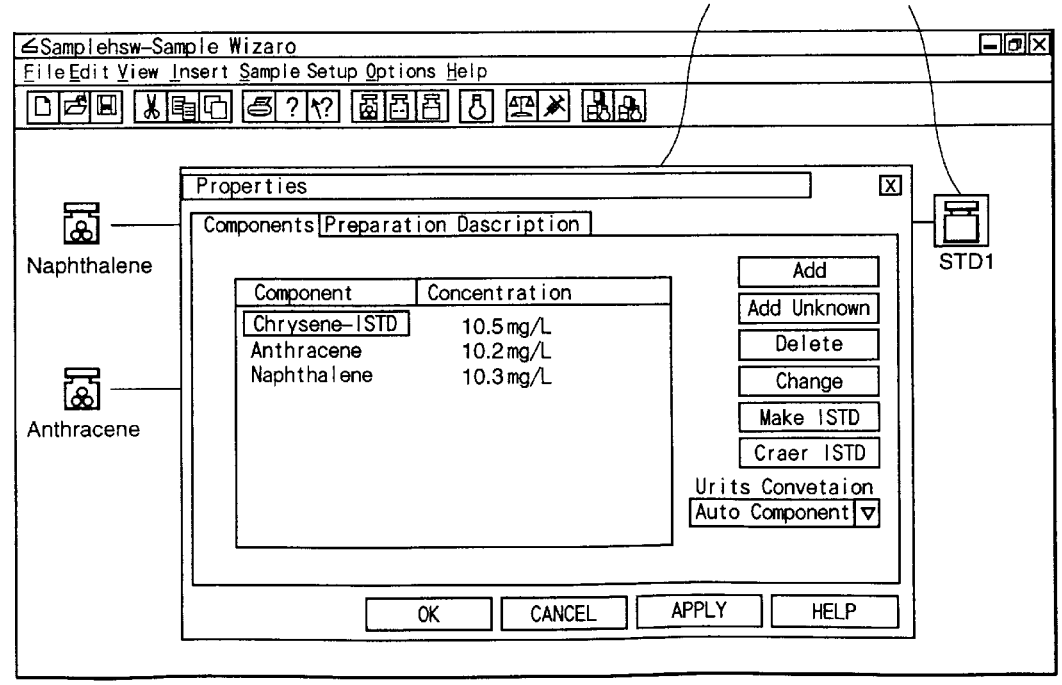
FIG. 6 is a diagram showing a detail data display screen for displaying detailed data on a sample.

With reference to FIG. 6, a detail display screen for a sample to be analyzed by liquid chromatograph will be described. Solution icon 17 depicts sample STD1 to be analyzed by the liquid chromatograph. When solution icon 17 in the preparation procedure input screen is double-clicked, detail display screen 21 is displayed. Concentrations of respective components displayed on this screen are not ones which were entered by the operator, but are such ones which were automatically computed from the weighed quantities, constant volumes, pipetting quantities and from the concentration of internal standard material, chrysence. In the case where this sample STD1 is analyzed by liquid chromatograph, the values of concentrations having been computed above are used for the result of an analysis in data processing unit 6.

Figure 7:
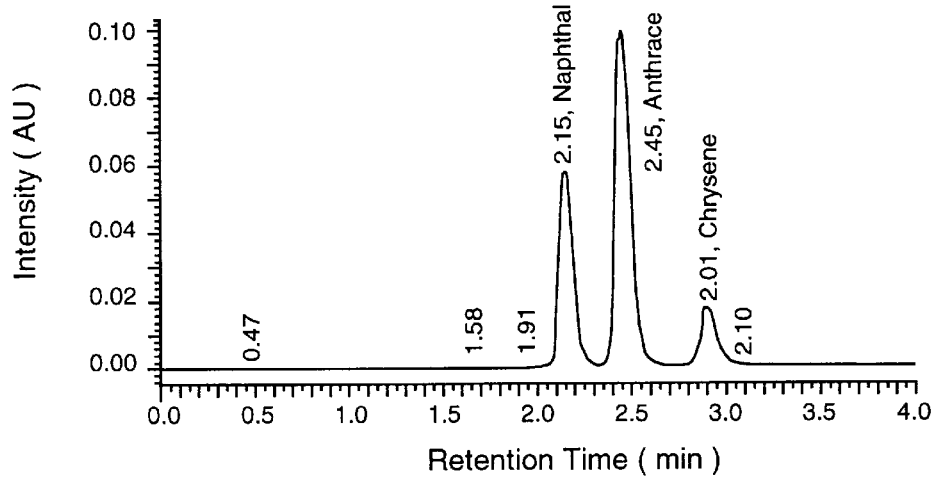
FIG. 7 is a diagram showing an example of output reports.
Figure 7:
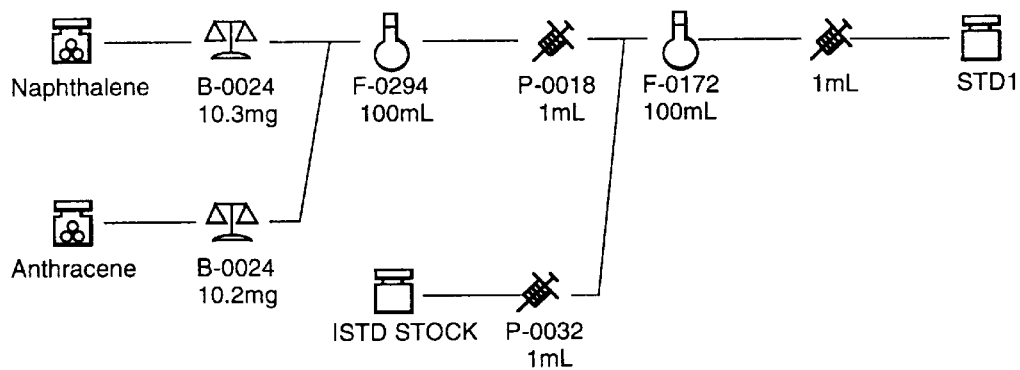

FIG. 7 shows an example of output reports produced by the liquid chromatograph after completion of analysis of the standard sample. Values of concentrations of respective components displayed here are ones which were automatically computed (naphthalene 10.3 mg/L, anthracene: 10.2 mg/L, chrysene: 10.5 mg/L). Respective sample preparation procedures are output, together with the result of analysis, as the "Sample Preparation Procedure" in a row of icons which were generated on the preparation procedure input screen.

Figure 8:
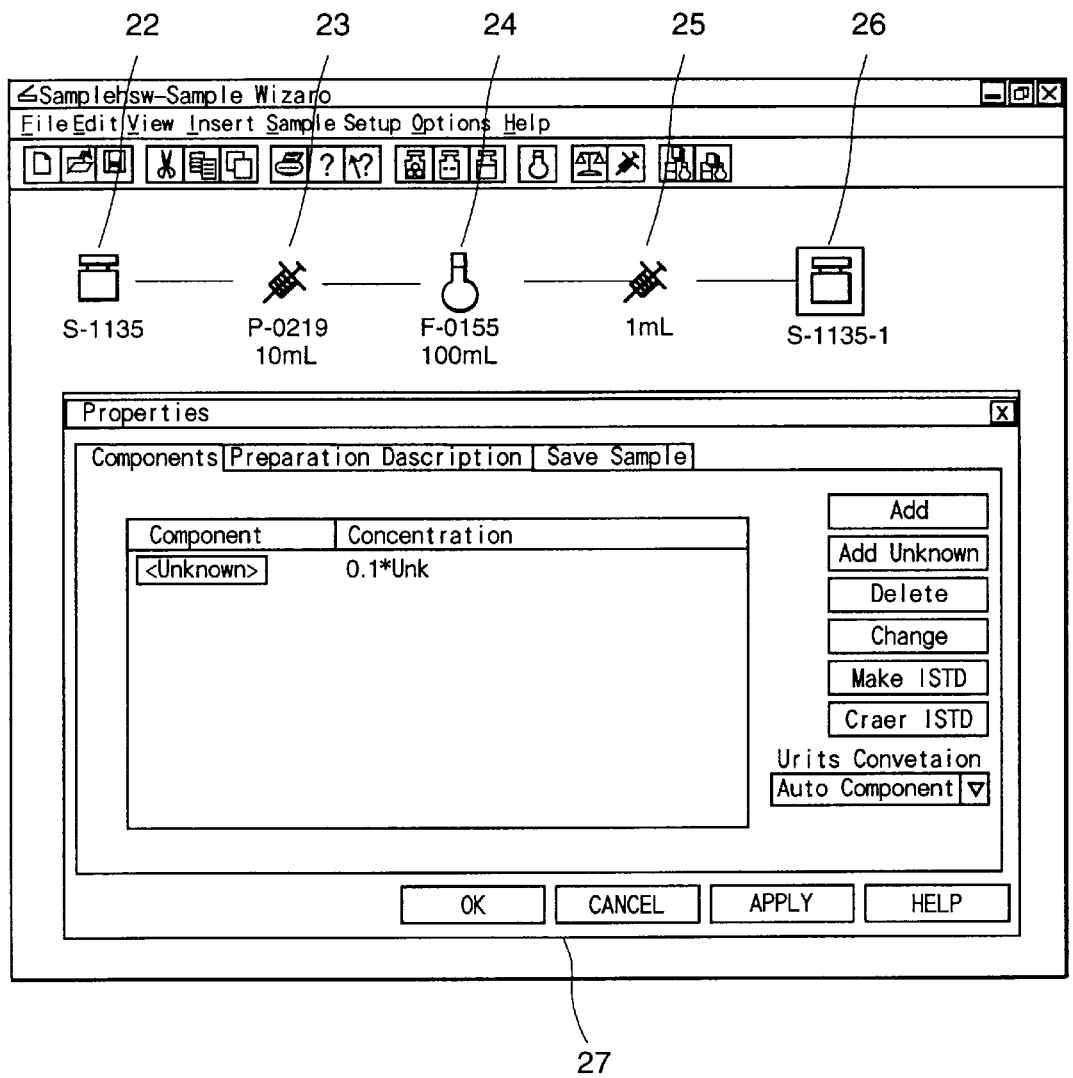
FIG. 8 is a diagram showing a sample preparation procedure input display screen for an unknown sample according to the invention.

Now, with reference to FIG. 8, an example screen of sample preparation procedures for an unknown sample will be described in the following. This procedure specifies that "10 ml of a target sample be injected in a measuring flask with a capacity of 100 ml, to be diluted with methanol to a constant volume of 100 ml, approximately 1 ml of which be injected into a sample bottle to be analyzed by liquid chromatograph."

Also on this unknown sample preparation procedure input screen, the same items are displayed as on the preparation procedure input screendused for the preparation of the above-mentioned standard sample. Namely, work items frequently used such as "weighing quantity", "constant volume dilution", "pipetting", "solution" and the like are expressed by icons. Each icon can open a brief operation detail display screen associated thereto also on this display screen, whereby necessary requirements can be entered for display through respective icons.

Icon 22 is a pictograph depicting a liquid sample, and is entered to be stored together with the sample name S-1138 which is an unknown sample. Icons 23 and 25 depict pippeting, and icon 24 depicts a constant volume dilution. Icon 26 depicts a liquid solution sample, and when it is double-clicked, window 27 of a detail display screen is displayed. On the detail display window of liquid solution sample 26, it is allowed to display the name of its component and its concentration. Concentration "0.1*Unk" displayed here is a value which is automatically computed from the values of pippeting and constant volume dilution, and it indicates that the unknown sample is diluted in this solution by 0.1 times.

Upon analysis of this sample S-1135-1 by the liquid chromatograph, a concentration of the unknown sample S-1135 is automatically computed by data processing unit 6 on the basis of a value of measurement obtained by analysis and a dilution ratio obtained from the above-mentioned data of the liquid sample. For example, in the case where as a result of analysis of sample S-1135-1 using the liquid chromatograph, a value of 5.56 mg/L is obtained as a concentration of naphthalene, it is then converted to a concentration of sample S-1135 and output as 55.6 mg/L (multiplied by 10, an inverse number of the dilution ratio) on the output report thereof. Therefore, it is only required for the operator to enter the values of pippetting, constant volume dilution and the like during the generation of the sample preparation procedure input display screen, thereafter, the value of concentration of the sample desired to be obtained after the analysis can be obtained automatically, thereby minimizing the human errors.

Further, as for the output reports, because the result of analysis and the rows of icons generated in the sample preparation procedure input screen are displayed on the same display window thereof (not shown), they can be easily traced. Also, by storing this report displayed on the window in a storage unit such as a hard disk or the like in data processing unit 6, it facilitates easy tracing afterward.

Figure 9:
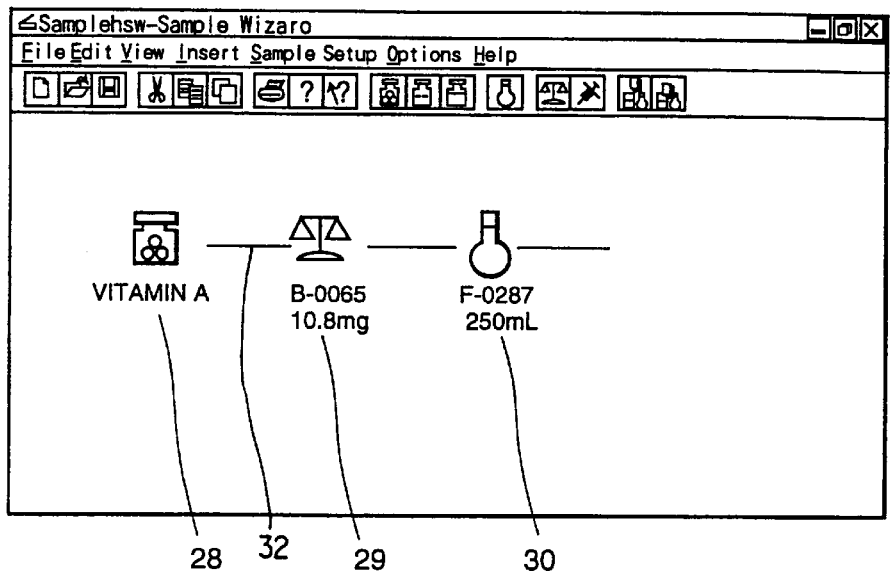
FIG. 9 is a diagram showing a sample preparation process on the preparation procedure input display screen.
Figure 10:
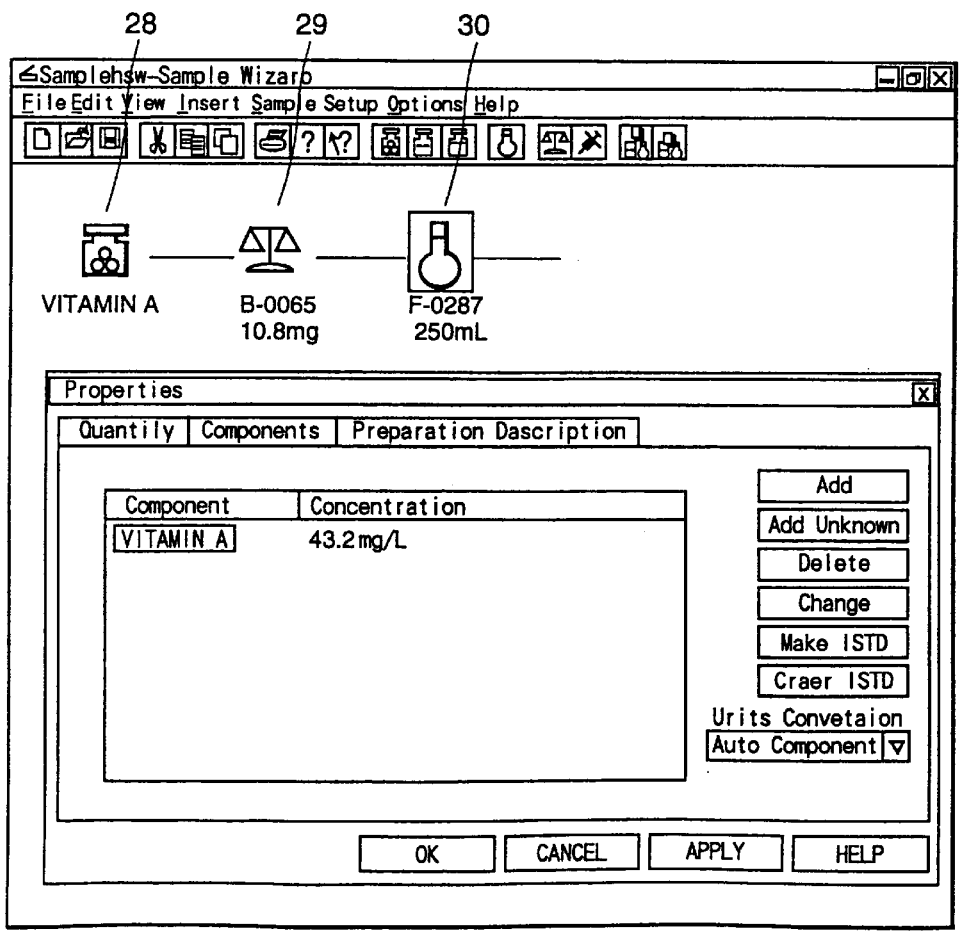
FIG. 10 is another diagram showing a sample preparation Process on the preparation procedure input display screen.

FIGS. 9 and 10 are examples indicating details of procedures for generating the row of icons on the window of the sample preparation procedure input screen.

Each icon depicts an entity or a unit operation. For example, in FIG. 10, icon 28 depicts an individual component (VITAMIN A), icon 29 depicts a weight measurement operation thereof (weighing 10.8 mg using balance B-0065), and icon 30 depicts a constant volume dilution operation thereof (dilution to a constant volume of 250 ml in measuring flask F-0287). On the sample preparation procedure input screen (window), these steps of operation are linked with a line to be input as a procedure. For example, by connecting icons 28, 29 and 30 with a line 32 in FIG. 10, a procedure is entered to specify that "10.8 mg of a component (VITAMIN A) be weighed, and diluted to a constant volume of 250 ml." In data processing unit 6, it is determined that operations represented by their respective icons connected by the line are to be executed in time sequences in order from left to right, thereby executing computation of concentration and the like, including processing for branching and convergence. This process is also executed in the same manner in the display window during the preparations of both the above-mentioned standard sample and the unknown sample. Therefore, when ion 30 is double-clicked, the concentration of VITAMIN A is automatically computed and displayed as 43.2 mg/L on the detail information display window 31.

According to the embodiments of the invention described hereinabove, the data processing unit 6 thereof is provided with the function to be able to enter the preparation procedures for the standard sample and the unknown sample, as well as the weighed value, injection value and constant dilution volume during the preparation thereof. Therefore, there is an advantage in that through entry of the sample preparation procedures before its sample pipetting, a quantity of contents in the standard sample and a dilution ratio of the unknown sample are automatically computed, thereby allowing the concentration of the unknown sample to be obtained from the result of the automatic computation. Further, in the data processing unit 6, the results of measurements are stored along with various conditions of the equipment at the time of the measurements (such as solution compositions and pump flow rate). Therefore, according to the analysis using the embodiment of the invention, traces of every pieces of data become easier to track down, from the preparation procedures including the manual handling method to the analysis by the liquid chromatograph.

Moreover, although the embodiments of the invention have been described above using the example of the analysis with the liquid chromatograph, it is not, however, limited thereto, and it should be construed in the same scope of the invention to apply to any other analytical apparatus in which data at the time of sample preparation will influence the result of its analysis.

Still further, in he case of analysis where its sample is prepared by the manual handling method, because the administration of the sample preparation procedure can be executed in association with the result of analysis by the analysis apparatus, the data having been entered at the time of the preparation can be reflected on the result of analysis when it is output, thereby eliminating the necessity of elaborate calculation and its time by the operator himself/herself. In addition, since the manual handling operation required for the operator is limited to the data entry during the preparation, it enables substantially to reduce the possibility of human errors.

Still further, because the sample preparation procedure by-the manual handling method-and the result of measurements by the analytical apparatus can be stored together associated therebetween, there is an advantage that the trace of data (i.e., evidence of sample history) becomes substantially easier. Still further, there is another advantage that thanks to the automatic computation on the basis of the weighed value, constant dilution volume and the like which were entered as procedural input values during the sample preparation, human errors are minimized, and analytical equipment which can obtain a highly reliable value of analysis can be provided.

What is claimed is:

1. An analyzer having an analytical unit for analyzing a sample which is prepared manually, a data processing unit for calculating an analysis result, and a display unit for displaying at least said analysis result, said display unit comprising:

a plurality of icons, each graphically representing a unit procedure required for preparing the sample;

a sample preparation procedure display region representing a sample preparation procedure by arranging each one of the plurality of icons;

a detail information display region for entering and displaying data associated with each of said icons relating to a target sample preparation procedure said detail information displav region being displayed when a corresponding icon is selected; and wherein said data processing unit uses the data entered through said detail information region in editing said analysis result.

2. An analyzer according to claim 1, wherein in the vicinity of each of a plurality of said icons displayed in said sample preparation procedure display region, there is displayed character data from said detail information display region.

3. An analyzer according to claim 1, wherein the plurality of said unit procedure regions displayed in said sample preparation procedure display region are connected with a connection line in a time series order of processing.

4. An analyzer according to claim 1, wherein, in a case where a sample to be prepared is a standard sample, said data processing unit executes computation of a concentration of the sample prepared using data which is entered through said detail information display region.

5. An analyzer according to claim 1, wherein said sample preparation procedure display region is displayed on said display unit together with said analysis result.

6. An analyzer according to claim 5, wherein said data processing unit stores said displayed sample preparation procedure display region and said displayed result of analysis therewith.

7. A method of liquid chromatograph analysis comprising the steps of:

preparing a sample;

feeding an eluting solution;

producing a mixture solution by mixing said sample in said eluting solution;

separating said mixture solution in a separation column;

detecting said mixture solution having passed through said separation column using a detector, displaying icons representative of at least one component to be analyzed and work performed thereon in preparing said sample so as to provide a sample preparation procedure;

entering information relating to said components to be analyzed or said work to be performed for each icon; and producing a result of analysis on the basis of said information having been entered and an output from said detector.

8. A liquid chromatograph analysis apparatus for analysis of a sample which is prepared in a set of serial steps including manual preparation comprising:

a pump for feeding a eluting solution;

a sample holder in which a sample having been prepared in at least one manual preparation step is mixed with said eluting solution having been fed so as to produce a mixture solution therebetween;

a separation column for separating said mixture solution into a series of individual components according to different respective retention time thereof; and a detector for detecting different components of the mixture solution having passed through said separation column;

a display unit which can display a representation of one or more of said serial steps required for the preparation of said sample distinct from each other on its screen;

an input device for entering information associated with said one or more steps having been displayed; and a processing unit which produces a result of analysis on the basis of said information having been entered and an output from said detector.

* * * * *

UNITED STATES PATENT AND TRADEMARK OFFICE
CERTIFICATE OF CORRECTION

PATENT NO. : 6,058,764
DATED : May 9, 2000
INVENTOR(S) : M. Fukuda et al.

It is certified that error appears in the above-identified patent and that said Letters Patent is hereby corrected as shown below:

On the Title Page,

Item [73]

Change "Hitachi, Ltd." to --Hitachi, Ltd.
                                      Hitachi Instruments Engineering Co., Ltd.--

Signed and Sealed this

Twenty-seventh Day of March, 2001

*Attest:*

NICHOLAS P. GODICI

*Attesting Officer*        *Acting Director of the United States Patent and Trademark Office*